United States Patent
Park et al.

(10) Patent No.: US 11,559,215 B2
(45) Date of Patent: Jan. 24, 2023

(54) METHOD FOR MEASURING HIGH-ACCURACY REALTIME HEART RATE BASED ON CONTINUOUS-WAVE DOPPLER RADAR AND RADAR SYSTEM THEREFOR

(71) Applicant: Korea Advanced Institute of Science and Technology, Daejeon (KR)

(72) Inventors: Seong Ook Park, Daejeon (KR); Junhyeong Park, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 333 days.

(21) Appl. No.: 16/577,957

(22) Filed: Sep. 20, 2019

(65) Prior Publication Data

US 2020/0155011 A1    May 21, 2020

(30) Foreign Application Priority Data

Nov. 20, 2018  (KR) .................. 10-2018-0143238
Jul. 30, 2019  (KR) .................. 10-2019-0092153

(51) Int. Cl.
  *A61B 5/024*  (2006.01)
  *A61B 5/00*  (2006.01)
  (Continued)

(52) U.S. Cl.
  CPC .......... *A61B 5/024* (2013.01); *A61B 5/7257* (2013.01); *A61B 5/7264* (2013.01); *A61B 8/488* (2013.01);
  (Continued)

(58) Field of Classification Search
  None
  See application file for complete search history.

(56) References Cited

U.S. PATENT DOCUMENTS 8,814,805 B2*  8/2014  Lin ................. A61B 5/1114
                                            600/534
9,870,457 B2*  1/2018  Lux ................. A61B 5/0507
(Continued)

FOREIGN PATENT DOCUMENTS

JP    2000-316825 A    11/2000
JP    2017-169868 A     9/2017
JP     2017169868 A *   9/2017

OTHER PUBLICATIONS

Park et al., "Polyphase-basis discrete cosine transform for real-time measurement of heart rate with CW Doppler radar". IEEE Transactions in Microwave Theory and Techniques, vol. 66, Issue: 3, pp. 1644-1659, Mar. 2018. Date of Publication: Nov. 28, 2017. (Year: 2017).*

(Continued)

*Primary Examiner* — Yi-Shan Yang
(74) *Attorney, Agent, or Firm* — Foley & Lardner LLP

(57) ABSTRACT

A method for measuring a high-accuracy and real-time heart rate based on a continuous-wave radar is provided. The method includes receiving an in-phase (I) signal and a quadrature (Q) signal for a receive signal received through the continuous-wave radar, selecting any one signal by comparing magnitudes of the received I signal and the received Q signal, performing frequency transform of each of bases respectively having predetermined phases with respect to the any one selected signal, and determining a heart rate based on a magnitude response of each of the bases by the frequency transform.

20 Claims, 14 Drawing Sheets

(51) Int. Cl.
*A61B 8/08* (2006.01)
*G01S 13/536* (2006.01)
*G06F 17/14* (2006.01)

(52) U.S. Cl.
CPC .......... *A61B 5/7225* (2013.01); *G01S 13/536* (2013.01); *G06F 17/147* (2013.01)

(56) References Cited

U.S. PATENT DOCUMENTS

| | | | |
|---|---|---|---|
| 2016/0191163 A1* | 6/2016 | Preston | H04B 10/2575 398/16 |
| 2016/0336989 A1* | 11/2016 | Lin | H04L 27/3881 |
| 2019/0158494 A1* | 5/2019 | Nakayama | A61B 5/117 |

OTHER PUBLICATIONS

Shin et al., "Adaptive threshold method for the peak detection of photoplethysmographic waveform", Computer in Biology and Medicine 39 (2009) 1145-1152. (Year: 2009).*

Park, et al., "Polyphase-Basis Discrete Cosine Transform for Real-Time Measurement of Heart Rate with CW Doppler Radar," *IEEE Transactions on Microwave Theory and Techniques*, vol. 66, No. 3, pp. 1644-1659 (Nov. 2017).

Office Action issued in Korean Patent Application No. 10-2019-0092153 dated Oct. 21, 2020, with English translation, fifteen (15) pages.

\* cited by examiner

METHOD FOR MEASURING HIGH-ACCURACY REALTIME HEART RATE BASED ON CONTINUOUS-WAVE DOPPLER RADAR AND RADAR SYSTEM THEREFOR

CROSS-REFERENCE TO RELATED APPLICATIONS

A claim for priority under 35 U.S.C. § 119 is made to Korean Patent Application No. 10-2018-0143238 filed on Nov. 20, 2018, and Korean Patent Application No. 10-2019-0092153 filed on Jul. 30, 2019, in the Korean Intellectual Property Office, the entire contents of which are hereby incorporated by reference.

BACKGROUND

Embodiments of the inventive concept described herein relate to technologies of measuring a heart rate using a continuous-wave Doppler radar, and more particularly, relate to a method for using a window of a short length and enhancing the accuracy of measuring a heart rate, using a polyphase basis discrete cosine transform (PB-DCT) to which DCT together with polyphase bases is applied and a radar system therefor.

Studies for detecting and analyzing cardiopulmonary movements using Doppler radar have been researched for many decades. Thanks to noncontact characteristics of the Doppler radar, there is no need to attach or detach the measurement auxiliary instrument from the body when inspecting heartbeat or respiration and there is no need to prepare and arrange the instruments. Furthermore, because there is no great loss when the electromagnetic wave penetrates clothing, patients do not need to takeoff clothes when measured. It could be helpful for patients suffering from burns, shingles, or complex regional pain syndrome, which should not be touched. Thanks to these advantages, studies for detecting and analyzing cardiopulmonary movements using the Doppler radar have continued to the present. There has been a growing demand to apply it to the real industry, for example, a medical bio-signal monitoring sensor and an bio-signal monitoring sensor for driver sleepiness prevention.

A continuous-wave Doppler radar with the characteristics of high sensitivity compared with the relatively simple system configuration is one of the types of radars primarily used in this field. Studies for measuring the heart rate in real time using the continuous-wave Doppler radar is one of the most recent issues in this field. The heart rate usually changes constantly, and sudden changes in heart rate occur in short time due to body internal and external factors. The heart rate should be measured to catch such a phenomenon and immediately determine the relationship with diseases or several physiological mechanisms.

There are two techniques used mainly in the signal processing method for measuring cardiopulmonary movements using the radar and computing the heart rate. One is a method called arctangent demodulation (AD) and the other is a method called complex signal demodulation (CSD). Because two methods are based on quadrature demodulation, they may resolve the null point problem which is the typical problem in this field. Furthermore, both the two methods have one thing in common that uses a peak-search method for using discrete Fourier transform (DFT) when transformed into the frequency domain, taking the absolute value after the transform, and analyzing the absolute value as the magnitude response to determine the frequency with the largest value in the heart rate range as the heart rate. In general, any method uses a window length of 10 seconds or more to enhance the resolution on the frequency spectrum.

There is an inverse relationship between the window length and main-lobe width (MLW) and side-lobe width (SLW) in the spectrum. Therefore, the longer the window length is, the shorter the MLW and the SLW are in the spectrum and the better the resolution is. In other words, the heartbeat signal, the respiration signal, and MLW and SLW of harmonic components and intermodulation components of these signals become short, and it is clear to classify the components. Due to this, as described above, the window length of 10 seconds or more is mainly used to increase the resolution in this field. In general, although real-time measurement is performed, the heart rate updated every several seconds is extracted by applying the sliding-window method using such a long window. However, technically, it cannot be called real-time measurement. Because of applying the long window, the past data is more dominant than the updated current data. In other words, although there is a momentary change in heart rate, because the rate of the amount of the past data on one window is snore dominant than the amount of the currently updated data, it is unable to sensitively inflect a change in heart rate in real time. Even so, when the window length is decreased, MLW and SLW of the above-mentioned components increase and the resolution problem of the spectrum occurs again. Thus, in the window length, there is the tradeoff between real-time measurement and resolution (the accuracy of measuring the heart rate).

There is a need for a technology capable of using the window of a short length and obtaining good spectrum resolution.

SUMMARY

Embodiments of the inventive concept provide a method for using a window of a short length and enhancing the accuracy of measuring a heart rate, using a polyphase basis discrete cosine transform (PB-DCT) to which DCT together with polyphase bases is applied and a radar system therefor.

According to an exemplary embodiment, a method for measuring a heart rate in real time based on a continuous-wave radar may include receiving an in-phase (I) signal and a quadrature (Q) signal for a receive signal received through the continuous-wave radar, selecting any one signal by comparing magnitudes of the received I signal and the received Q signal, performing frequency transform of each of bases respectively having predetermined phases with respect to the any one selected signal, and determining a heart rate based on a magnitude response of each of the bases by the frequency transform.

The method may further include performing zero-phase digital filtering of the received I signal and the received Q signal. The selecting may include selecting the any one signal by comparing magnitudes of the I signal and the Q signal in which the zero-phase digital filtering is performed.

The performing of the frequency transform may include performing discrete cosine transform (DCT) of each of the bases.

The determining of the heart rate may include determining a frequency for the largest magnitude response among magnitude responses of each of the bases as the heart rate.

The determining of the heart rate may include extracting magnitude responses of each of the bases, collecting maximum values and frequency information through peak searching in a predetermined heart rate range, and determining a frequency with the largest value among the maximum values as the heart rate.

The performing of the frequency transform may include performing fast Fourier transform (FFT) on the any one selected signal and performing discrete transform of each of the bases respectively having the phases with respect to the any one signal in which the FFT is performed.

The performing of the frequency transform may include applying the phases to a basis for the any one selected signal and performing discrete transform on each of the bases respectively having the phases.

The performing of the frequency transform may include enhancing resolution of a heartbeat signal in a frequency spectrum obtained by performing discrete transform by multiplying the any one selected signal by bases to which the phases are applied.

According to an exemplary embodiment, a method for measuring a heart rate in real time based on a continuous-wave radar may include performing frequency transform of each of bases respectively having predetermined phases with respect to any one signal between an I signal and a Q signal for a receive signal received through the continuous-wave radar and determining a heart rate based on the result of performing the frequency transform of each of the bases.

The performing of the frequency transform may include selecting any one signal by comparing magnitudes of the I signal and the Q signal and performing discrete transform of each of the bases with respect to the any one selected signal.

The performing of the frequency transform may include performing zero-phase digital filtering of the I signal and the Q signal, selecting the any one signal by comparing magnitudes of the I signal and the Q signal in which the zero-phase digital filtering is performed, and performing discrete transform on each of the bases with respect to the any one selected signal.

The determining of the heart rate may include extracting magnitude responses of each of the bases, collecting maximum values and frequency information through peak searching in a predetermined heart rate range, and determining a frequency with the largest value among the maximum values as the heart rate.

The performing of the frequency transform may include performing FFT of the any one signal and performing discrete transform of each of the bases respectively having the phases with respect to the any one signal in which the FFT is performed.

According to an exemplary embodiment, a radar system may include a baseband receiving unit that removes a common mode direct current (DC) component and common ode noise from each of an I signal and a Q signal and a signal processing unit that performs frequency transform of each of bases respectively having predetermined phases with respect to any one signal between the I signal and the Q signal output from the baseband receiving unit.

The baseband receiving unit may remove the common mode DC component and the common mode noise by passing each of the I signal and the Q signal through an instrumentation amplifier.

The signal processing unit may select any one signal by comparing magnitudes of the I signal and the Q signal and may perform discrete transform of each of the bases with respect to the any one selected signal.

The signal processing unit may perform zero-phase digital filtering of the I signal and the Q signal, may select the any one signal by comparing magnitudes of the I signal and the Q signal in which the zero-phase digital filtering is performed, and may perform discrete transform of each of the bases with respect to the any one selected signal.

The signal processing unit may extract magnitude responses of each of the bases, may collect maximum values and frequency information through peak searching in a predetermined heart rate range, and may determine a frequency with the largest value among the maximum values as the heart rate.

The signal processing unit may perform FFT on the any one signal and may perform discrete transform on each of the bases respectively having the phases with respect to the any one signal in which the FFT is performed.

The signal processing unit may enhance resolution of a heartbeat signal in a frequency spectrum obtained by performing discrete transform by multiplying the any one selected signal by bases to which the phases are applied.

According to an exemplary embodiment, an apparatus for measuring a heart rate in real time based on a continuous-wave radar may include a reception unit that receives an I signal and a Q signal for a receive signal received through the continuous-wave radar, a selection unit that selects any one signal by comparing magnitudes of the received I signal and the received Q signal, a transform unit that performs frequency transform for each of bases respectively having predetermined phases with respect to the any one selected signal, and a determination unit that determines a heart rate based on a magnitude response of each of the bases by the frequency transform.

The reception unit may perform zero-phase digital filtering on the received I signal and the received Q signal. The selection unit may select the any one signal by comparing magnitudes of the I signal and the Q signal in which the zero-phase digital filtering is performed.

The transform unit may perform DCT of each of the bases.

The determination unit may determine a frequency for the largest magnitude response among magnitude responses of each of the bases as the heart rate.

The determination unit may extract magnitude responses of each of the bases, may collect maximum values and frequency information through peak searching in a predetermined heart rate range, and may determine a frequency with the largest value among the maximum values as the heart rate.

The transform unit may perform FFT on the any one selected signal and may perform discrete transform of each of the bases respectively having the phases with respect to the any one signal in which the FFT is performed.

The transform unit may apply the phases to a basis for the any one selected signal and may perform discrete transform on each of the bases respectively having the phases.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
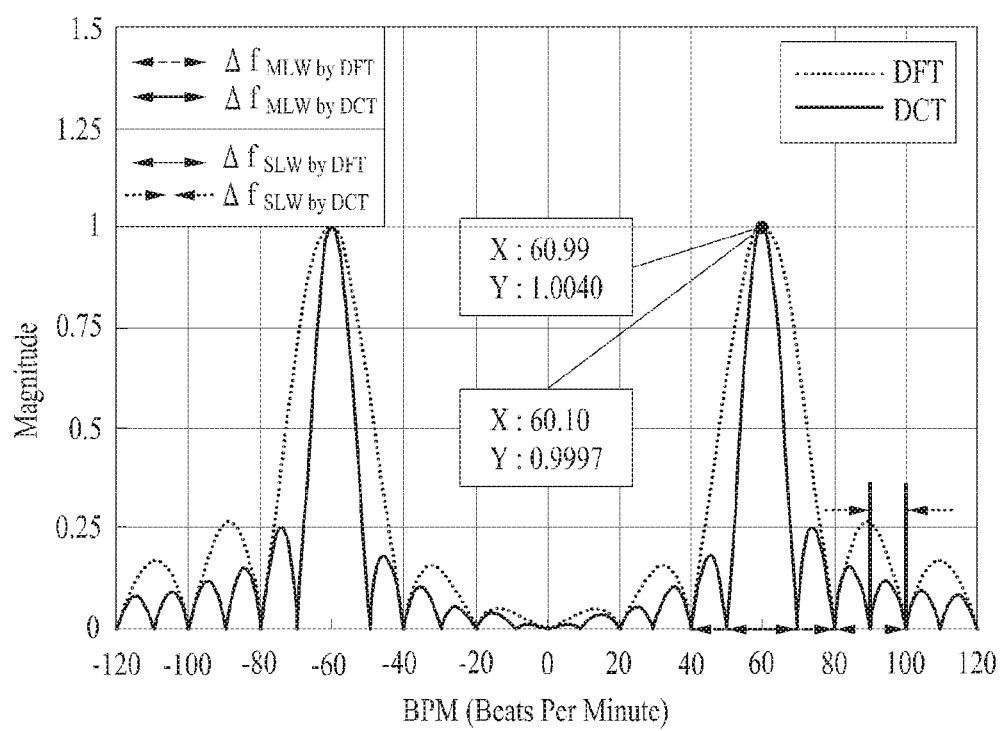
FIG. 1 is a drawing illustrating an example of comparing MLW and SLW obtained by the result of performing discrete cosine transform (DCT) used in an embodiment of the inventive concept with MLW and SLW obtained by the result of discrete Fourier transform (UPI)

Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other components, steps, operations, and/or elements other than stated, components, steps, operations, and/or elements but do not exclude presence of additional elements.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

Hereinafter, a description will be given in detail of exemplary embodiments of the inventive concept with reference to the accompanying drawings. Like reference numerals are used for the same components shown in each drawing, and a duplicated description of the same components will be omitted.

Embodiments of the inventive concept are the gist of using a window of a short length and enhancing the accuracy of measuring a heart rate by using polyphase basis discrete cosine transform (PB-DCT) to which DCT together with polyphase bases is applied.

In this case, embodiments of the inventive concept may reduce main-lobe width (MLW) and side-lobe width (SLW) in the spectrum by half by using the PB-DCT, thus obtaining good spectrum resolution in spite of using a short window length.

The default basis of the DCT applied in embodiments of the inventive concept has a newly defined form to effectively address the existing problems, rather than typical basis forms of the DCT, which are generally known.

Hereinafter, a description will be given in detail of embodiments of the inventive concept with reference to Equations and the accompanying drawings.

In general, the N-point discrete Fourier transform (DPT) used to find out a frequency component of the discrete-time signal x[n] may be represented as Equation 1 below.

$$X_{DFT}[k] = \sum_{n=0}^{L-1} x[n]e^{-j\frac{2\pi k}{N}n} \quad \text{[Equation 1]}$$

Herein, L is the number of discrete-time signal samples. Thus, N-L refers to the number of zero samples for zero padding. n and k denote the discrete time domain and the discrete frequency domain, respectively.

$$e^{-j\frac{2\pi k}{N}n}$$

is the basis, and $X_{DFT}[k]$ is the result of performing the N-point DFT of x[n]. The modulated signal into which information about cardiopulmonary movements is loaded in the reception basis unit of the continuous-wave radar may be represented as the series of the sine periodic signals. When putting x[n] in a simple cosine signal for convenience of development, an embodiment of the inventive concept may represent Equation 1 above as Equation 2 below.

$$X_{DFT}[k] = \sum_{n=0}^{L-1} A \frac{e^{j\omega_0 n} + e^{-j\omega_0 n}}{2} e^{-j\frac{2\pi k}{N}n} \quad \text{[Equation 2]}$$

Herein, A and $\omega_0$ refer to the amplitude and angular frequency of x[n] respectively.

Considering a situation close to the continuous spectrum with a sufficient number of N, Equation 2 above may be represented as Equation 3 below.

$$X_{DFT}(e^{j\omega}) = \frac{A}{2}\sum_{n=0}^{L-1} (e^{-j(\omega-\omega_0)n} + e^{-j(\omega+\omega_0)n}) \quad \text{[Equation 3]}$$

Finally, Equation 3 above may be developed as Equation 4 below.

$$X_{DFT}(e^{j\omega}) = \frac{A}{2}\left\{\left(e^{\frac{-j(\omega-\omega_0)(L-1)}{2}} \frac{\sin\left(\frac{(\omega-\omega_0)L}{2}\right)}{\sin\left(\frac{\omega-\omega_0}{2}\right)}\right) + \left(e^{\frac{-j(\omega+\omega_0)(L-1)}{2}} \frac{\sin\left(\frac{(\omega+\omega_0)L}{2}\right)}{\sin\left(\frac{\omega+\omega_0}{2}\right)}\right)\right\} \quad \text{[Equation 4]}$$

Herein, the left term represents a desired signal and the right term represents an image signal.

The solution of the left term indicating the desired signal may be represented as Equation 5 below.

$$\omega = \omega_0 + \frac{2m\pi}{L}, \quad m = \pm 1, \pm 2, \pm 3, \ldots \quad \text{[Equation 5]}$$

Thus, MLW which is the frequency domain length of the main lobe representing the signal and SLW which is the frequency domain length of the side lobe may be represented as Equation 6 below.

$$\Delta\omega_{MLW\ by\ DFT} = \omega|_{m=1} - \omega|_{m=-1} = \frac{4\pi}{L} \quad \text{[Equation 6]}$$
$$\Delta\omega_{SLW\ by\ DFT} = \omega|_{m=2} - \omega|_{m=1} = \frac{2\pi}{L}$$

When expressing Equation 6 above in the real frequency range, Equation 6 above may finally be represented as Equation 7 below.

$$\Delta f_{MLW\ by\ DFT} = \frac{2F_S}{L} = \frac{2}{T}, \Delta f_{SLW\ by\ DFT} = \frac{F_S}{L} = \frac{1}{T} \quad \text{[Equation 7]}$$

Herein, Fs refers to the sampling frequency, and T refers to the window length.

Therefore, as described above, because an embodiment of an inventive concept basically peruses real time, when the window length is decreased, MLW and SLW increase.

Equation 8 below represents DCT defined in an embodiment of the inventive concept.

$$X_{DCT}[k] = 2\sum_{n=0}^{L-1} x[n]\cos\left(\frac{2\pi k}{N}n\right) \quad \text{[Equation 8]}$$

As may be observed in Equation 8 above, the new type of basis $$\cos\left(\frac{2\pi k}{N}n\right)$$

different from types of bases in DCT which is generally known is used. Considering a situation close to the continuous spectrum with a sufficient number of N by putting the discrete-time signal in the simple cosine signal in the same manner as inducing MLW and SLW in DFT, Equation 8 above may be represented as Equation 9 below.

$$X_{DCT}(e^{j\omega}) = \quad \text{[Equation 9]}$$
$$\frac{A}{2}\sum_{n=0}^{L-1}\left(e^{j(\omega+\omega_0)n} + e^{-j(\omega-\omega_0)n} + e^{j(\omega-\omega_0)n} + e^{-j(\omega+\omega_0)n}\right)$$

Finally, Equation 9 above may be expressed as Equation 10 below.

$$X_{DCT}(e^{j\omega}) = A\left\{\left(\frac{\cos\left(\frac{(\omega-\omega_0)(L-1)}{2}\right)\sin\left(\frac{(\omega-\omega_0)L}{2}\right)}{\sin\left(\frac{\omega-\omega_0}{2}\right)}\right) + \left(\frac{\cos\left(\frac{(\omega+\omega_0)(L-1)}{2}\right)\sin\left(\frac{(\omega+\omega_0)L}{2}\right)}{\sin\left(\frac{\omega+\omega_0}{2}\right)}\right)\right\} \quad \text{[Equation 10]}$$

Herein, the left term is a desired signal, and the right term is an image signal.

The solution of the left term indicating the desired signal may be represented as Equation 11 below.

$$\omega = \begin{cases} \frac{(2m+1)\pi}{L-1} + \omega_0, & m = \text{All integers} \\ \frac{2n\pi}{L} + \omega_0, & n = \pm 1, \pm 2, \pm 3, \ldots \end{cases} \quad \text{[Equation 11]}$$

Therefore, MLW which is the frequency domain length of the main lobe representing the signal and SLW which is the frequency domain length of the side lob may be represented as Equation 12 below.

$$\Delta f_{MLW\ by\ DCT} = \frac{F_S}{L} = \frac{1}{T}, \Delta f_{SLW\ by\ DCT} = \frac{F_S}{2L} = \frac{1}{2T} \quad \text{[Equation 12]}$$

When expressing Equation 12 above in the real frequency range, Equation 12 above may finally be represented as Equation 13 below.

$$\Delta f_{MLW\ by\ DCT} = \frac{F_S}{L} = \frac{1}{T}, \Delta f_{SLW\ by\ DCT} = \frac{F_S}{2L} = \frac{1}{2T} \quad \text{[Equation 13]}$$

When comparing Equation 7 above with Equation 13 above, it may be mathematically proved that the MLW and SLW due to the DCT newly defined in an embodiment of the inventive concept is half the MLW and SLW due to the DCT.

FIG. 1 is a drawing illustrating an example of comparing MLW and SLW obtained by the result of performing DCT used in an embodiment of the inventive concept with MLW and SLW obtained by the result of discrete Fourier transform (DFT ). X axis indicates beats per minute (BPM) converted by multiplying the frequency Hz by 60. FIG. 1 illustrates results of taking the absolute value of the result of Equations 1 and 8 with respect the cosine signal, which has the used sampling frequency of 100 Hz, the window length of 3 s, the amplitude of which is 1 and the frequency of which is 1 Hz, that is, 60 BPM, and multiplying a suitable constant to express Y axis as the magnitude value.

As may be observed in FIG. 1, MLW and SLW are about 40 BPM and about 20 BPM, respectively, in the case of DFT, whereas MLW and SLW are about 20 BPM and about 10 BPM, respectively, in the case of DCT in an embodiment of the inventive concept. It may be seen that MLW and SLW in the DCT in an embodiment of the inventive concept are reduced by half as compared with those in the DFT. By applying the peak-search method, seeing BPM information indicated by a point where a magnitude response value of each transform is the maximum, it may be verified that the DCT in an embodiment of the inventive concept has a more accurate value than the DEL This is because side lobes of an image signal have less influence on a main lobe of a desired signal thanks to the reduced SLW.

The relationship like Equation 14 below may be derived between the DCT according to an embodiment of the inventive concept and the general DE1.

$$X_{DCT}[k] = 2\sum_{n=0}^{L-1} x[n]\cos\left(\frac{2\pi k}{N}n\right) \qquad \text{[Equation 14]}$$
$$= \sum_{n=0}^{L-1} x[n]e^{-j\frac{2\pi k}{N}n} + \sum_{n=0}^{L-1} x[n]e^{j\frac{2\pi k}{N}n}$$
$$= X_{DFT}[k] + X^*_{DFT}[k] = 2\text{Re}\{X_{DFT}[k]\}$$

When actually implemented, DFT is mainly implemented using fast Fourier transform (FFT) to obtain the advantage of fast computation. By Equation 14 above, because it is able to implement the DCT according to an embodiment of the inventive concept by taking a real part in the DFT and multiplying the real part by the factor 2, when the DCT according to an embodiment of the inventive concept is actually implemented, it is able to implement the DCT according to the embodiment of the inventive concept by using the fast computation of the FFT.

When receiving signals including information about cardiopulmonary movements using a radar and when finally collecting the signals in the window, considering a situation applied to actually calculating a heart rate because there is always a random phase at that time, the DCT according to an embodiment of the inventive concept is applicable like Equation 15 below.

$$X_{DCT}[k] = 2\sum_{n=0}^{L-1} A \cos(\omega_0 n + \alpha)\cos\left(\frac{2\pi k}{N}n + \beta\right) \qquad \text{[Equation 15]}$$

Herein, $\alpha$ denotes the phase of the signal finally input to the window, and $\beta$ denotes the phase of the cosine basis determined by the designer.

Finally, Equation 15 above may be represented as Equation 16 below.

[Equation 16]
$$X_{DCT}(e^{j\omega}) =$$
$$A\left\{\left(\frac{\cos\left(\frac{(\omega-\omega_0)(L-1)}{2} + \beta - \alpha\right)\sin\left(\frac{(\omega-\omega_0)L}{2}\right)}{\sin\left(\frac{\omega-\omega_0}{2}\right)}\right) + \left(\frac{\cos\left(\frac{(\omega+\omega_0)(L-1)}{2} + \beta + \alpha\right)\sin\left(\frac{(\omega+\omega_0)L}{2}\right)}{\sin\left(\frac{\omega+\omega_0}{2}\right)}\right)\right\}$$

Herein, the left term is a desired signal, and the right term is an image signal. The solution of the left term indicating the desired signal may be represented as Equation 17 below.

$$\omega = \begin{cases} \frac{(2m+1)\pi - 2(\beta-\alpha)}{L-1} + \omega_0, & m = \text{All integers} \\ \frac{2n\pi}{L} + \omega_0, & n = \pm 1, \pm 2, \pm 3, \ldots \end{cases} \qquad \text{[Equation 17]}$$

The magnitude value at the frequency $\omega_0$ of the input signal in the left term may be represented as Equation 18 below.

$$|X_{DCT}(e^{j\omega_0})| = AL|\cos(\beta-\alpha)| \qquad \text{[Equation 18]}$$

In other words, the shape of the spectrum may be changed depending on $\alpha$ and $\beta$, and errors may occur in the heart rate value. Thus, it is difficult to enhance the real-time computation of the heart rate from simply applying the DCT.

According to Equation 18 above, when the mathematical condition of Equation 19 below is established, the magnitude value at the frequency of the input signal may be the maximum.

$$\beta-\alpha=m\pi,\ m=0,\pm1,\pm2,\pm3,\ldots \qquad \text{[Equation 19]}$$

Figure 2A:
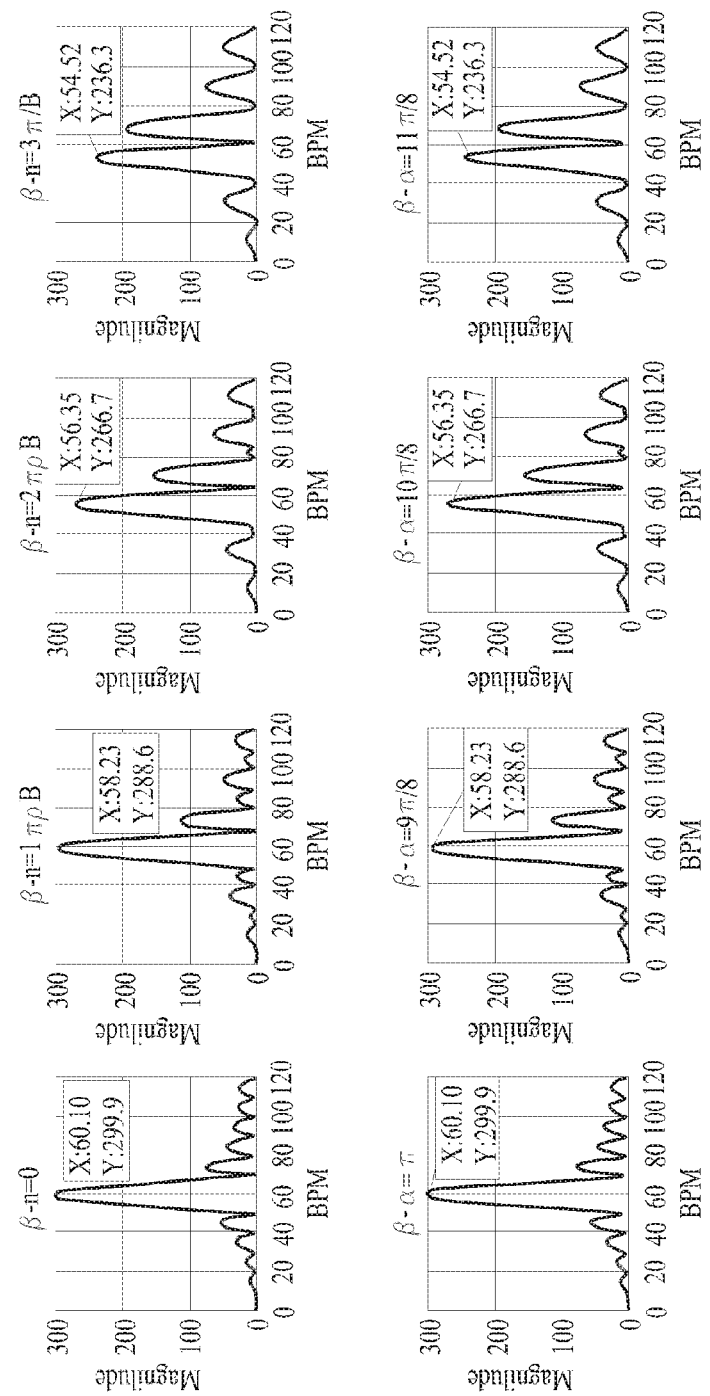
FIG. 2A and 2B are a drawing illustrating an example of the result of Equations 18 and 19.
Figure 2B:
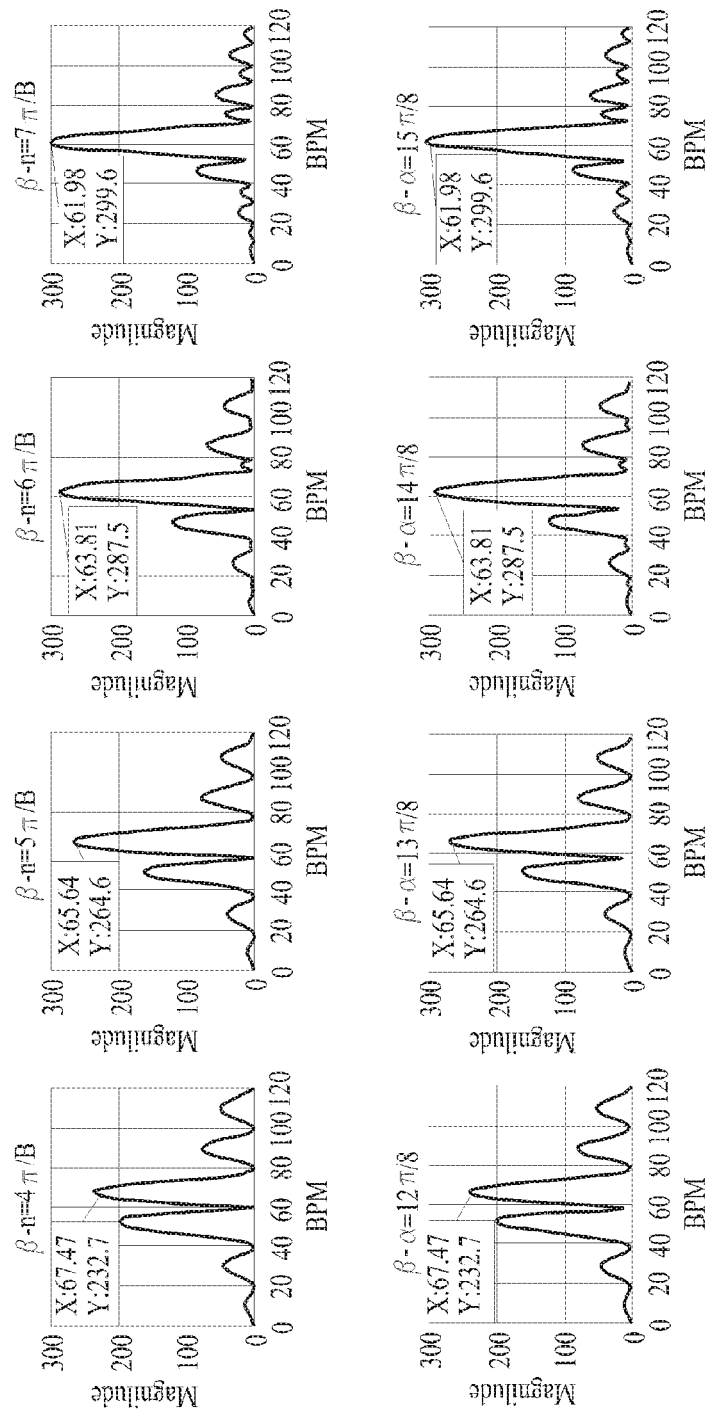

FIG. 2A and 2B are a drawing illustrating an example of the result of Equations 18 and 19. FIG. 2A and 2B illustrate applying the signal situation like FIG. 1 and separately failing to perform scaling such that the magnitude value at the input frequency follows Equation 18 above.

As may be observed in FIG. 2A and 2B, due to the period of the magnitude response capable of being derived from Equation 18 above, the magnitude response may be the same when $\beta-\alpha$ is $\pi$. As analyzed in conjunction with Equation 19 above, when $\beta-\alpha$ is 0 and $\pi$, it may be verified that the magnitude value at the frequency of the input signal is closest to the maximum value. In this case, as there is no distortion in the shape of the spectrum and as the errors are close to 0, the PB-DCS in an embodiment of the inventive concept may exploit such features.

Figure 3:
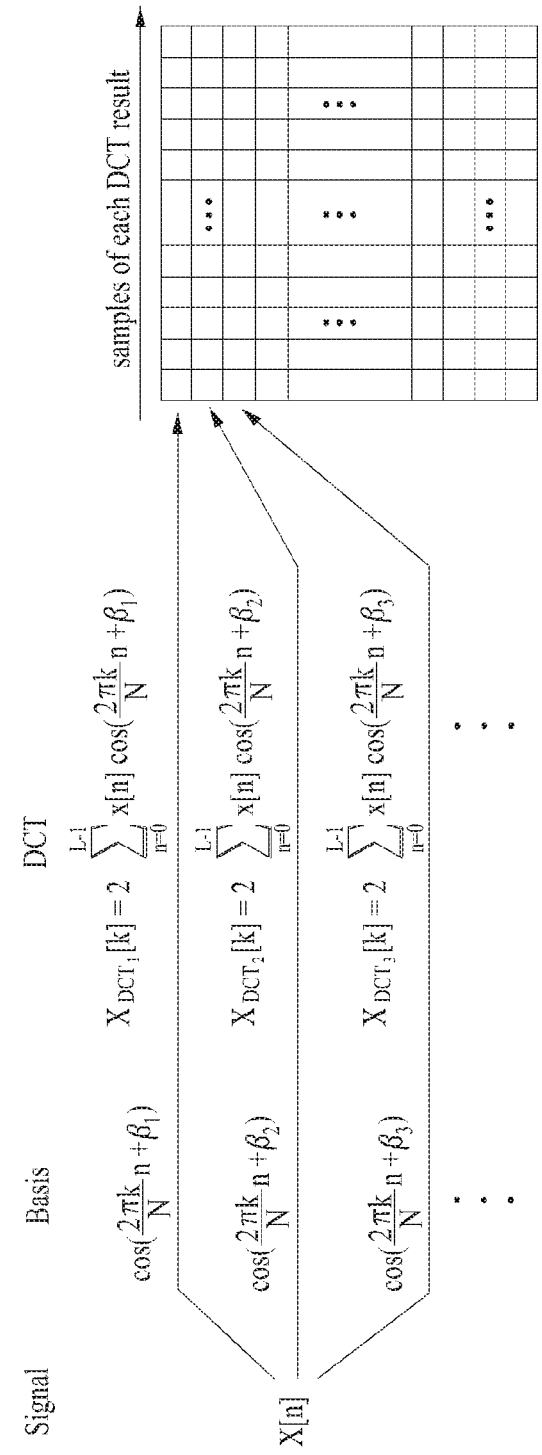
FIG. 3 is a drawing illustrating the concept of polyphase basis discrete cosine transform (PB-DCT)

FIG. 3 is a drawing illustrating the concept of PB-DCT. When a heart rate is computed in real time, the DCT of each of bases respectively having different phases may be performed for the signal input to the window of the short length.

In other words, as shown in FIG. 3, the phase such as the polyphase, for example, $\beta1$, $\beta2$, $\beta3$, and the like, may be applied to the basis $\cos(2\pi kn/n)$ to perform DCT ($X_{DCT1}$, $X_{DCT2}$, $X_{DCT2}$, and the like) of x[n] in parallel based on the bases. In the table for expressing the samples of the DCT results, the left first row in the top row is $X_{DCT1}[1]$ and the subsequent row is $X_{DCT2}[2]$. Likewise, the left first row in the second row is $X_{DCT2}[1]$ and the subsequent row is $X_{DCT2}[2]$. As such, an embodiment of the inventive concept may perform the PB-DCT of a basis defined in the embodiment of the inventive concept, that is, $\cos(2\pi kn/n)$.

Figure 4:
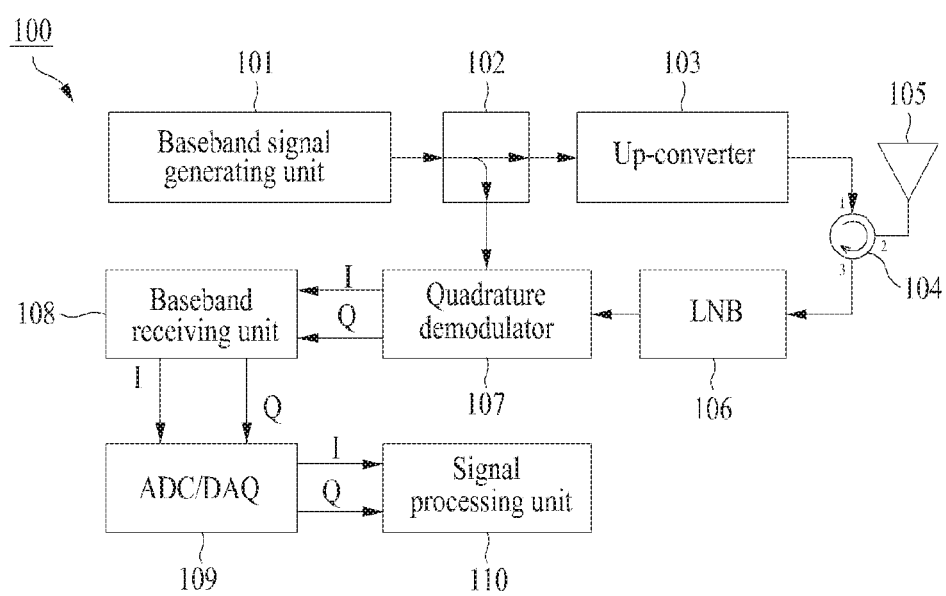
FIG. 4 is a block diagram illustrating a configuration of a continuous-wave Doppler radar system according to an embodiment of the inventive concept.

FIG. 4 is a block diagram illustrating a configuration of a continuous-wave Doppler radar system according to an embodiment of the inventive concept. FIG. 4 illustrates a configuration of a continuous-wave Doppler radar system for measuring cardiopulmonary movements.

Referring to FIG. 4, in the continuous-wave Doppler radar system according to an embodiment of the inventive concept, when a baseband signal generating unit 101 generates a continuous-wave signal, as one output port may be connected to an up-converter 103 via a power splitter 102 to convert the continuous-wave signal into a radio frequency (RF) frequency band to substantially transmit the continuous-wave signal. Another output port may be used when the received signal is down-converted and is finally converted into the baseband. The signal passing through the up-converter 103 may be transmitted to a target to be measured, for example, the chest of a person to be measured, via a circulator 104 and an antenna 105.

The reflected signal including information about cardiopulmonary movements may be received via the antenna 105, and the received signal may be greatly amplified together with characteristics of low noise via a low noise block (LNB) 106 to reduce the noise figure of the entire receive stage and may be down-converted in frequency. A quadrature demodulator 107 may quadrature-demodulate the signal output from the other port of the power splitter 102 and the signal output via the LNB 106 to be down-converted into the baseband and may concurrently output an in-phase (I) signal and a quadrature (Q) signal. A baseband receiving unit 108 may pass each of the I signal and the Q signal through an instrumentation amplifier to remove a received unnecessary common mode direct current (DC) component and common mode noise and to concurrently amplify a necessary signal. Thereafter, high-frequency noises may be attenuated through an active low pass filter (LPF), and the attenuated signal may be sampled by an analog-to-digital converter/data acquisition (ADC/DAQ) 109 to be stored as data. Finally, a signal processing unit 110 may calculate a heart rate in real time using the method according to an embodiment of the inventive concept.

In detail, the signal processing unit 110 may attenuate high-frequency noise and the respiration signal by applying zero-phase digital filtering using an infinite-duration impulse response (IIR) low pass filter (LPF) and IIR high pass filter (HPF), may compare the variances (or magnitudes) of the I signal and the Q signal to resolve the null point problem and may select a larger signal, may perform PB-DCT of the selected signal using bases respectively having different phases, and may compare the magnitude responses (or spectrums) to determine the frequency with the largest value as the finally calculated heart rate.

Figure 5:
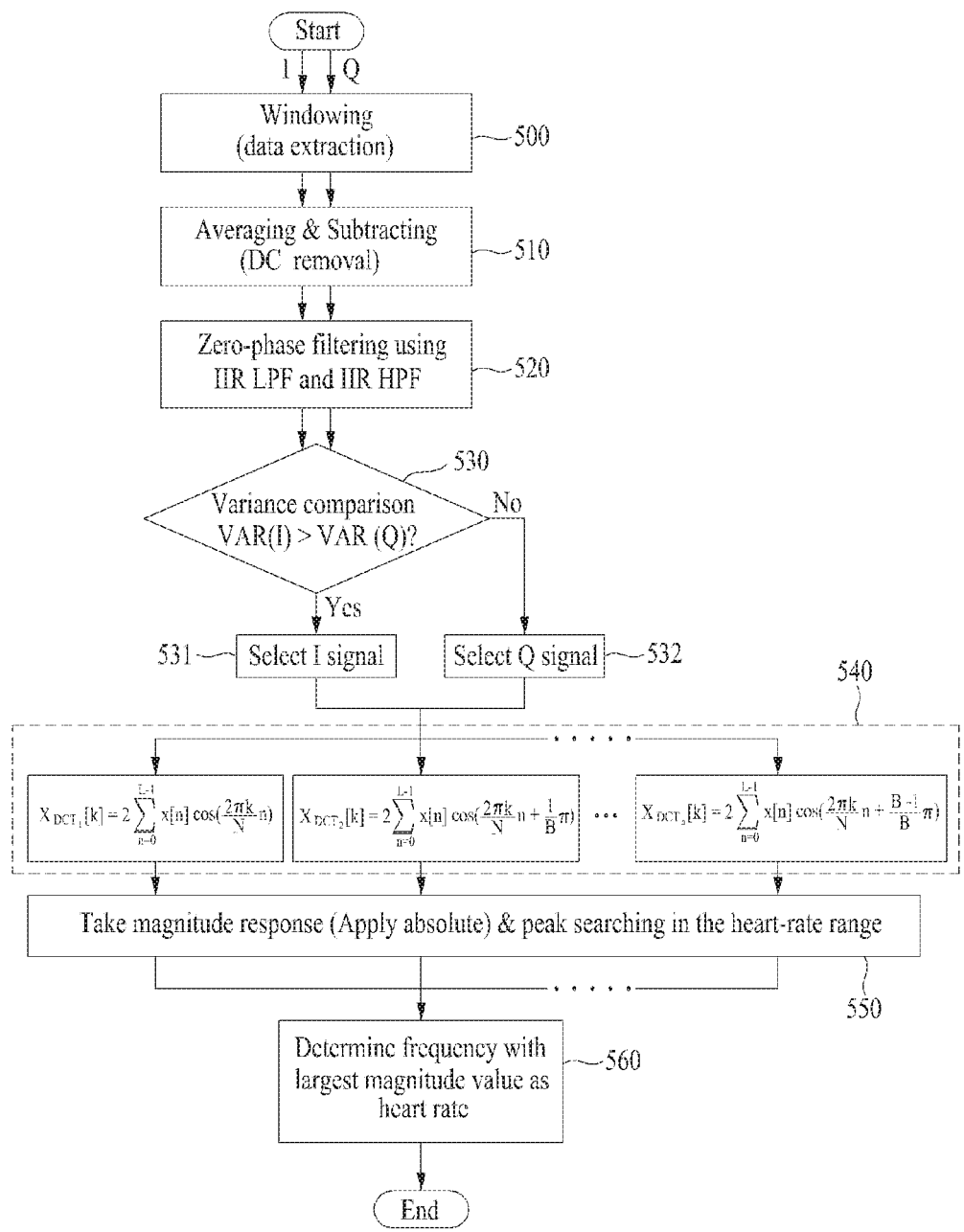
FIG. 5 is a flowchart illustrating an operation of a method for measuring a heart rate in real time according to an embodiment of the inventive concept.
Figure 6:
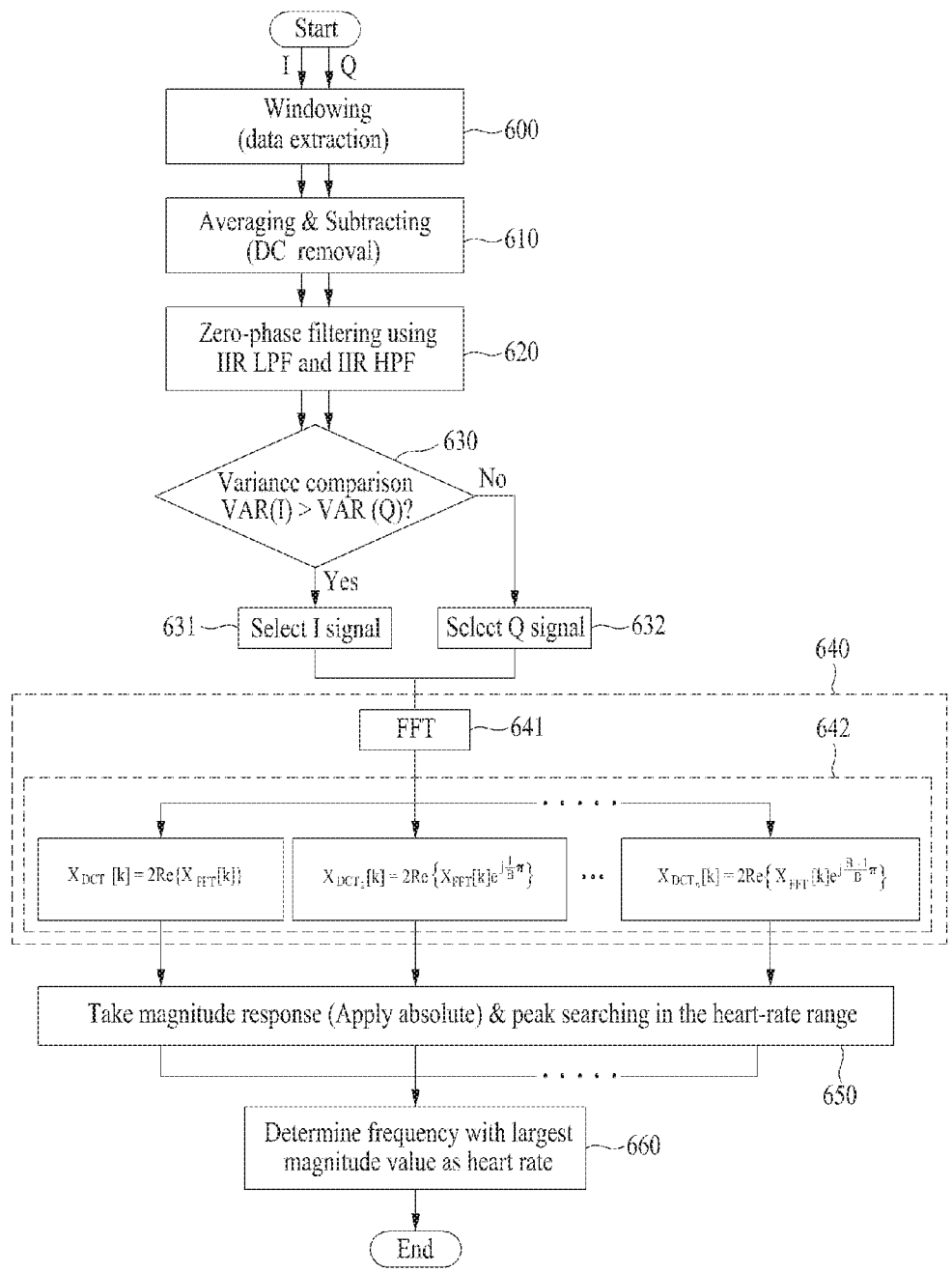
FIG. 6 is a flowchart illustrating an operation of a method for measuring a heart rate in real time according to another embodiment of the inventive concept.

A description will he given in detail of an operation of such a signal processing unit 110 with reference to FIGS. 5 and 6.

FIG. 5 is a flowchart illustrating an operation of a method for measuring a heart rate in real time according to an embodiment of the inventive concept. FIG. 6 is a flowchart illustrating an operation of a method for measuring a heart rate in real time according to another embodiment of the inventive concept. FIGS. 5 and 6 are flowcharts illustrating an operation of a signal processing unit 100 of FIG. 4.

Herein, FIG. 5 illustrates the entire processing algorithm for effectively applying PB-DCT. FIG. 6 illustrates an algorithm capable of the advantage of fast processing when actually implementing PB-DCT.

Referring to FIGS. 5 and 6, in a method for measuring a heart rate in real time according to embodiments of the inventive concept, when data is received at any one time during real-time processing on the window through windowing in operation 500 or 600, in operation 510 or 610, a DC component of the data may be removed by averaging the received data and subtracting the value from the data.

After the DC component is removed in operation 510 or 610, in operation 520 or 620, the high-frequency noise and the respiration signal may be filtered by applying zero-phase digital filtering using the IIR LPF and the IIR HPF. In this case, the IIR filter may be implemented in a lower order compared with the same performance than the finite-duration impulse response (FIR) filter and may prevent a phenomenon which is delayed or distorted in phase, using zero-phase digital filtering. There is the null point problem which is the typical issue in which the intensity of the signal is greatly attenuated depending on the distance between the antenna and the chest in this field. However, when any one of the I signal and the Q signal is close to the null point to be greatly attenuated, the other signal may be close to the optimum point to achieve the maximum intensity.

An embodiment of the inventive concept may resolve the null point problem by comparing the intensity of the I signal with the intensity of the Q signal and selecting a larger signal. In detail, in operation 530 or 630, an embodiment of the inventive concept may compare the variance of the I signal with the variance of the Q signal to compare the intensity of the I signal with the intensity of the Q signal. In operation 531 and 631 or 531 and 632, an embodiment of the inventive concept may select a larger signal.

Herein, in operation 530 or 630, variance comparison may be performed using that the variance of the signal is the AC power of the signal. When the intensity of the I signal is larger than the intensity of the Q signal through the comparison, in operation 531 or 631, die I signal may be selected. When the intensity of the Q signal is larger than the intensity of the I signal, in operation 532 or 632, the Q signal may be selected.

When the I signal or the Q signal is selected through the magnitude comparison, as described above, in operation 540, the PB-DCT of the selected signal may be performed using polyphase bases respectively having different phases.

Herein, like operation 540, in operation 640, the PB-DCT may be implemented at high speed by first performing FFT in operation 641 without the necessity of performing DCT separately per basis and loading and multiplying phases which are previously determined according to the result into the complex exponential function and extracting only a real part in operation 642.

In this case, an embodiment of the inventive concept may enhance the resolution of the heartbeat signal in the frequency spectrum obtained by performing discrete transform by multiplying the selected signal by bases to which the respective phases are applied.

Because the magnitude response is the same when $\beta-\alpha$ is $\pi$ thanks to the period in Equation 18 above, it is able to consider bases in only the range of 0 to $\pi$ without the necessity of considering the bases in the range of 0 to $2^\pi$ when selecting the bases. Because the phase of the input signal is completely random, when the bases are put at an equal interval in the range of 0 to $\pi$, a heart rate may be most reliably determined. The more the number of bases is, the more accurate the result may be. However, in operation 540 or 640, it is suitable to put bases by the number of bases (B bases) most suitable for real-time processing in consideration of processing performance of a signal processor.

In operation 550 or 560, the absolute value of respective results of DCT, output as a result of operation 540 or 640, may be taken to obtain magnitude responses and the maximum magnitude value and frequency information with the value may be collected through peak searching in the heartbeat frequency range from the respective magnitude responses. For example, when there are a total of 8 bases as a polyphase basis, PB-DCT of each of the 8 bases may be performed and the absolute values of the result values in which the PB-DCT is performed may be taken to obtain a total of 8 magnitude responses.

In operation 560 or 660, a frequency value having the largest magnitude value among the maximum magnitude value and information of the frequency having the value, collected through peak searching in the heartbeat frequency range from the collected magnitude responses, may be determined as a heart rate which is finally calculated. As shown in FIG. 2A and 2B, this may be based on the fact that the error of the frequency is the minimum when the magnitude value is largest.

Figure 7A:
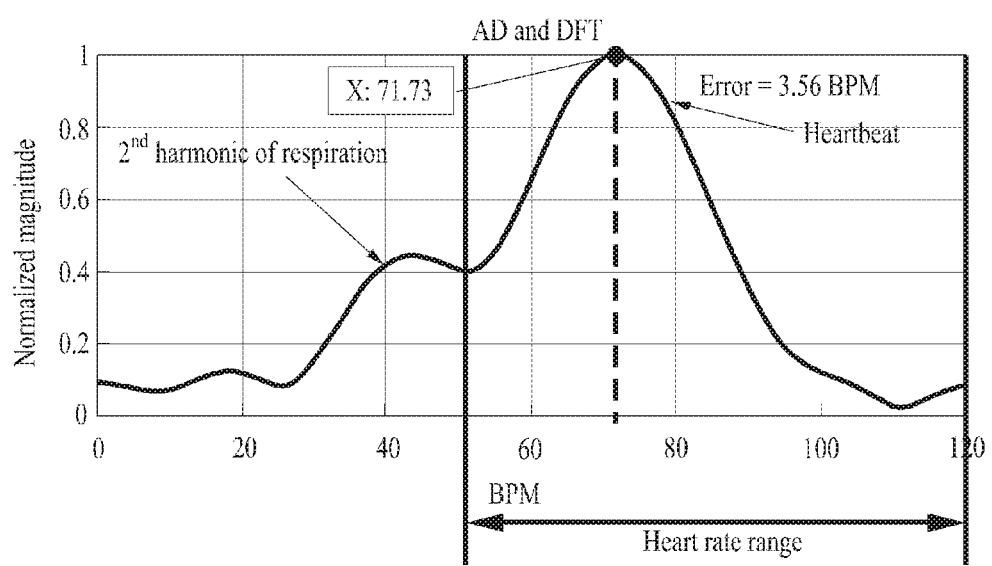
FIGS. 7A, 7B, and 7C are drawings illustrating results and errors of the spectrum by the existing methods and a method according to an embodiment of the inventive concept, when measuring cardiopulmonary movements in a general situation using a Doppler radar.
Figure 7B:
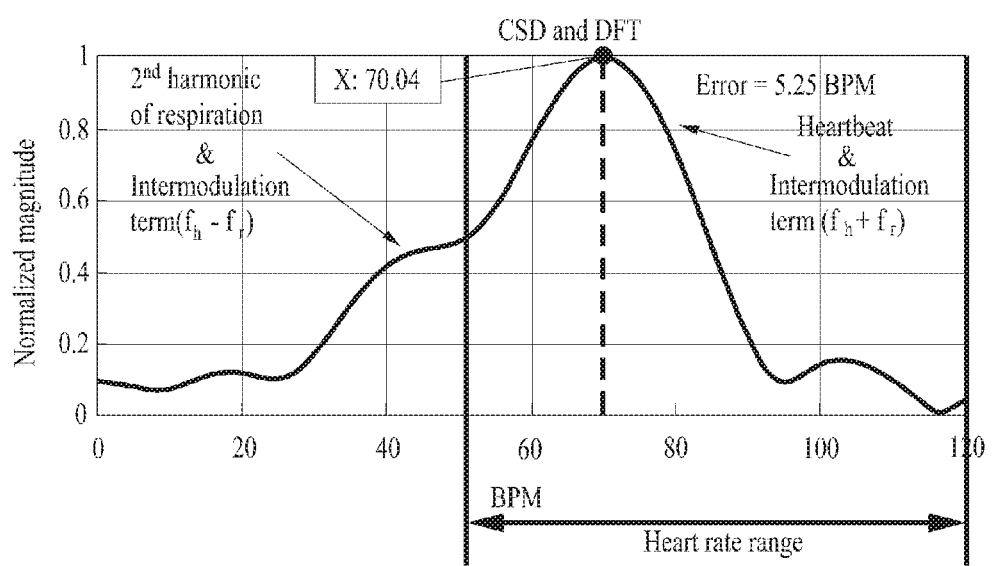
Figure 7C:
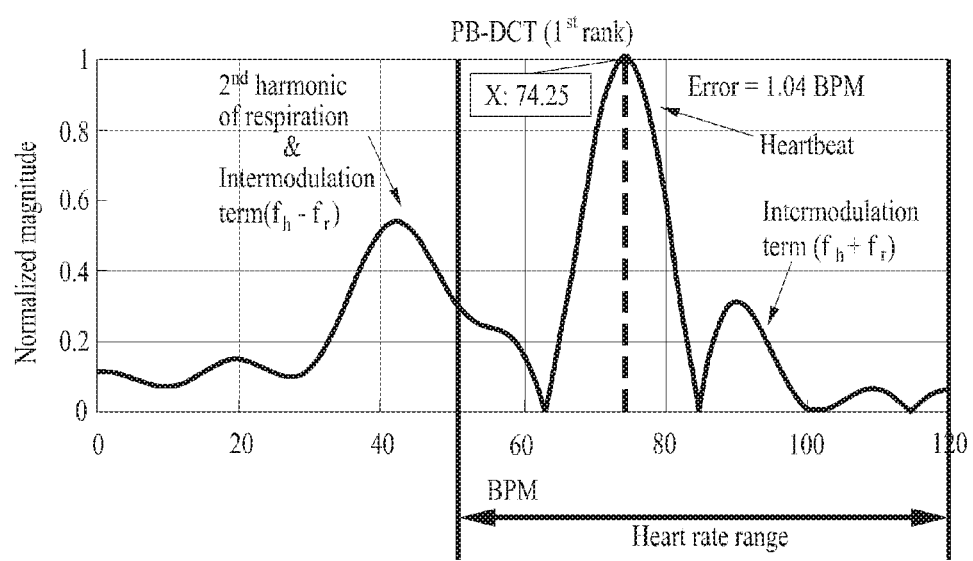

FIGS. 7A to 7C are drawings illustrating results and errors of the spectrum by the existing methods and a method according to an embodiment of the inventive concept, when measuring cardiopulmonary movements in a general situation using a Doppler radar.

As shown in FIGS. 7A and 7B, because MLW and SLW become wide because of a short window length in the existing methods, the heartbeat signal may be overlapped with the harmonic component of the respiration signal and intermodulation signals of the heartbeat-respiration signal. Due to this, in the existing methods, an error may greatly occur and it is difficult to distinguish signals. On the other hand, as shown in FIG. 7C, in the method according to an embodiment of the inventive concept, because MLW and SLW are reduced by half as compared with the existing methods, the resolution may be increased and respective components may be well distinguished to verify that the error of the calculated heart rate is small. Herein, in the situation of FIG. 7C, the true value of the heart rate may be 75.29 BPM.

Figure 8A:
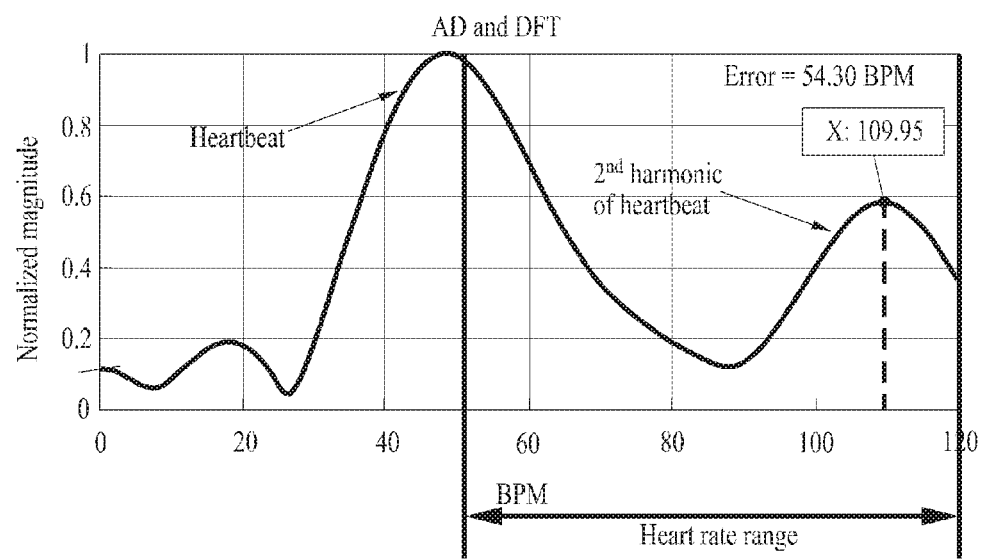
FIGS. 8A, 8B, and 8C are drawings illustrating results and errors of the spectrum by the existing methods and a method according to an embodiment of the inventive concept, when measuring cardiopulmonary movements in a specific situation using a Doppler radar.
Figure 8B:
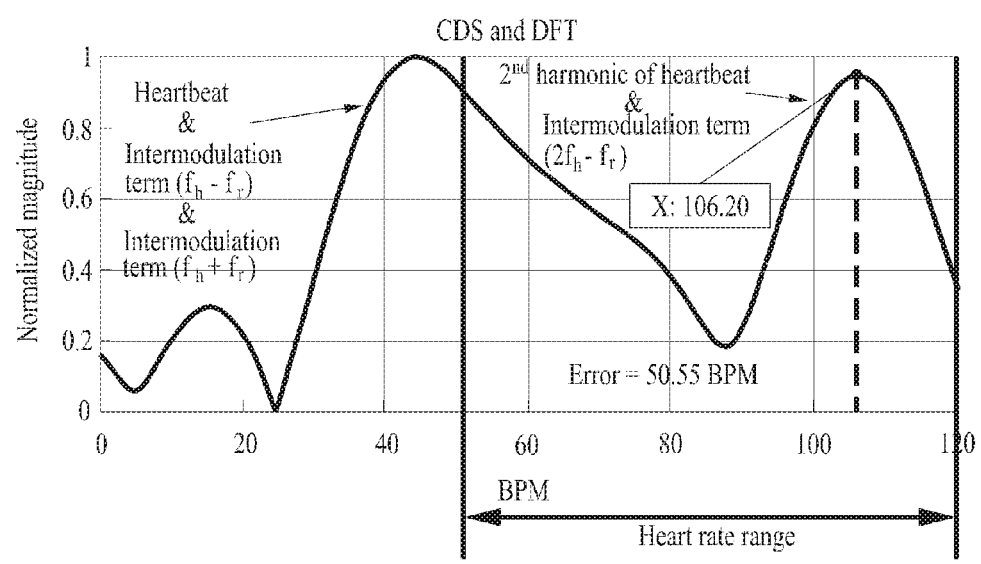
Figure 8C:
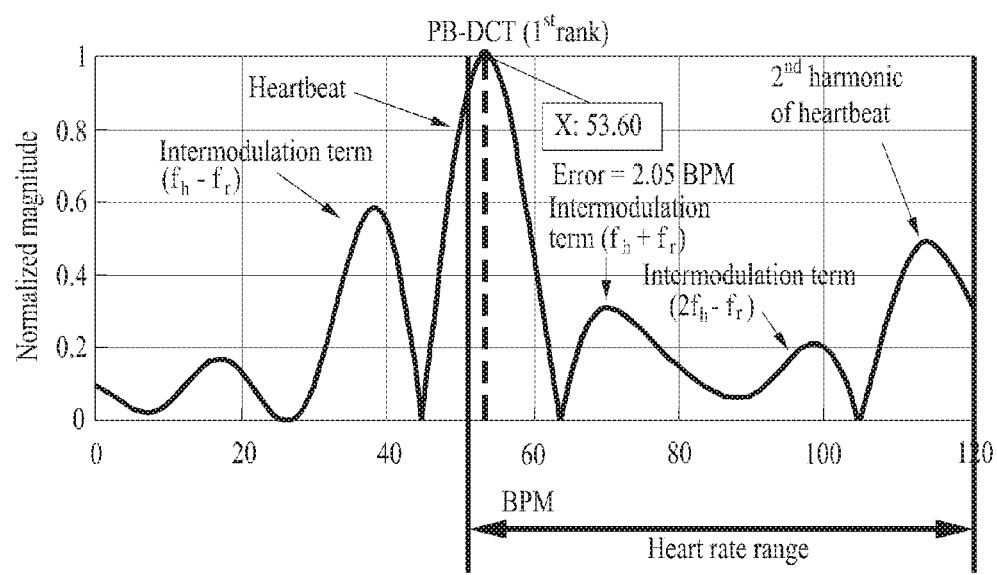

FIGS. 8A to 8C are drawings illustrating results and errors of the spectrum by the existing methods and a method according to an embodiment of the inventive concept, when measuring cardiopulmonary movements in a specific situation using a Doppler radar. FIGS. 8A to 8C illustrate results and errors of the spectrum processed by the existing methods and a method according to an embodiment of the inventive concept when cardiopulmonary movements are measured using a Doppler radar in the situation where the heart rate is low at about 50 to 60 BPM.

Such a low heart rate state mainly happens to athletes, and frequently happens to ordinary persons when they are measured while lying down at night.

As shown in FIGS. 8A and 8B, in the existing methods, the heartbeat signal is overlapped with undesirable signals and is pushed out from the heart-rate range. It is able to maximally attenuate the respiration signal itself in the range of 50 BPM or less, but the second harmonic component of the respiration signal and the heartbeat-respiration intermodulation signal ($f_h$-$f_r$) may have an influence due to the limit of the HPF. Therefore, when the heartbeat signal deviates from 50 BPM or less, it is difficult to determine the heartbeat signal. In addition, when the heart rate is low, because the second harmonic component of the heartbeat signal exists in the normal heartbeat range, the second harmonic component of the heartbeat signal may be determined as the heartbeat signal when actually applied. As such, an error should be very increased in the existing methods. On the other hand, as shown in FIG. 8C, in the method according to an embodiment of the inventive concept, due to MLW and SLW reduced by half, likewise FIG. 7C, the signal components are may not overlapped and may be well distinguished to verify that the error of the calculated heart rate is small. Herein, in the situation of FIG. 8C, the true value of the heart rate may be 55.65 BPM.

Figure 9:
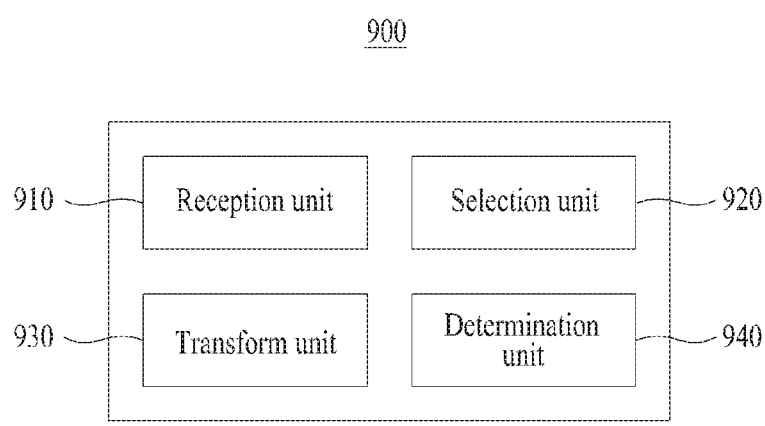
FIG. 9 is a block diagram illustrating a configuration of art apparatus for measuring a heart rate in real time according to an embodiment of the inventive concept.

FIG. 9 is a block diagram illustrating a configuration of an apparatus for measuring a heart rate in real time according to an embodiment of the inventive concept. FIG. 9 illustrates a configuration of a signal processing unit 110 of FIG. 4.

Referring to FIG. 9, an apparatus 900 for measuring a heart rate in real time according to an embodiment of the inventive concept may include a reception unit 910, a selection unit 920, a transform unit 930, and a determination unit 940.

The reception unit 910 may receive an I signal and a Q signal for a receive signal received through a continuous-wave radar.

Herein, the reception unit 910 may receive the I signal and the Q signal output through a baseband receiving unit 108 and an ADC/DAQ 1.09 of FIG. 4.

In this case, the reception unit 910 may perform digital zero-phase digital filtering of the received I signal and the received Q signal.

The selection unfit 920 may select any one signal through magnitude comparison, for example, variance comparison, between the received I signal and the received Q signal.

The transform unit 930 may perform discrete transform, for example, DCT, of each of bases respectively having predetermined phases with respect to the any one selected signal.

In this case, the transform unit 930 may perform FFT of the any one selected signal and may perform DCT of each of the bases respectively having the phases with respect to the any one signal in which the FFT is performed.

The determination unit 940 may determine a heart rate based on the magnitude response of each of the bases by the discrete transform.

In this case, the determination unit 940 may determine the frequency for the largest magnitude response among magnitude responses of each of the bases as the heart rate. In detail, the determination unit 940 may extract magnitude responses of each of the bases, may collect maximum values and frequency information through peak searching in a predetermined heart rate range, and may determine a frequency having the largest value among the maximum values as the heart rate.

It is apparent to those skilled in the art that, although the description is omitted in the apparatus of FIG. 9, the respective components configuring FIG. 9 may include all details described in FIGS. 1 to 8C.

An embodiment of the inventive concept is exemplified as the polyphase bases and the DCT for the method, the system, and the apparatus according to the embodiment of the inventive concept. However, embodiments of the inventive concept are not limited thereto. For example, the method, the system, and the apparatus according to the embodiment of the inventive concept may include all of discrete transform capable of combining the polyphase bases to perform discrete transform. In addition, the method, the system, and the apparatus according to an embodiment of the inventive concept are not limited to the discrete transform, and the method, the system, and the apparatus according to the embodiment of the inventive concept may include all of frequency transform capable of combining the polyphase bases to perform frequency transform.

The foregoing systems or devices may be realized by hardware elements, software elements and/or combinations thereof. For example, the systems, devices, and components illustrated in the exemplary embodiments of the inventive concept may be implemented in one or more general-use computers or special-purpose computers, such as a processor, a controller, an arithmetic logic unit (ALU), a digital signal processor, a microcomputer, a field programmable array (FPA), a programmable logic unit (PLU), a microprocessor or any device which may execute instructions and respond. A processing unit may implement an operating system (OS) or one or software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. Also, the processing unit may have a different processing configuration, such as a parallel processor.

Software may include computer programs, codes, instructions or one or more combinations thereof and may configure a processing unit to operate in a desired manner or may independently or collectively control the processing unit Software and/or data may be permanently or temporarily embodied in any type of machine, components, physical equipment, virtual equipment, computer storage media or units or transmitted signal waves so as to be interpreted by the processing unit or to provide instructions or data to the processing unit. Software may be dispersed throughout computer systems connected via networks and may be stored or executed in a dispersion manner. Software and data may be recorded in one or more computer-readable storage media.

The methods according to the above-described exemplary embodiments of the inventive concept may be implemented with program instructions which may be executed through various computer means and may be recorded in computer-readable media. The media may also include, alone or in combination with the program instructions, data files, data structures, and the like. The program instructions recorded in the media may be designed and configured specially for the exemplary embodiments of the inventive concept or be known and available to those skilled in computer software. Computer-readable media include magnetic media such as hard disks, floppy disks, and magnetic tape; optical media such as compact disc-read only memory (CD-ROM) disks and digital versatile discs (DVDs); magneto-optical media such as floptical disks; and hardware devices that are specially configured to store and perform program instructions, such as read-only memory (ROM), random access memory (RAM), flash memory, and the like. Program instructions include both machine codes, such as produced by a compiler, and higher level codes that may be executed by the computer using an interpreter. The described hardware devices may be configured to act as one or more software modules to perform the operations of the above-described exemplary embodiments of the inventive concept, or vice versa.

According to embodiments of the inventive concept, the apparatus for measuring the heart rate in real time may use a window of a short length and may enhance the accuracy of measuring the heart rate by using the PB-DCT based on the continuous-wave Doppler radar. Thus, an embodiment of the inventive concept may reduce MLW and SLW in the spectrum by half and may obtain good spectrum resolution in spite of using the short window length.

In other words, when using the short window length, main lobes (MLs) side lobes (SLs) of several frequency components are overlapped in the existing methods to degrade resolution and increase the error, whereas an embodiment of the inventive concept may reduce the error by effectively dividing frequency components due to MLW and SLW reduced by half and may thus measure a heart rate accurately.

An embodiment of the inventive concept is applicable to almost all of continuous-wave radars for measuring a heart rate in real time and is applicable to the fields associated with preventing the drowsiness of drivers and checking the states of the drivers as well as medical circles such as hospitals for monitoring heart rates of patients using the continuous-wave radars. For example, an embodiment of the inventive concept is applicable to the auto industry, the civil/military industry associated with technologies of checking states of pilots or civil aircraft pilots, several transportation companies which serve health conditions of passengers to the passengers, life-saving in disaster situations, and the like.

An embodiment of the inventive concept may measure a heart rate in real time and may be implemented by only digital signal processing.

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Therefore, other implements, other embodiments, and equivalents to claims are within the scope of the following claims.

What is claimed is:

1. A method for measuring a heart rate in real time based on a continuous-wave radar, the method comprising:
receiving an in-phase (I) signal and a quadrature (Q) signal for a receive signal received through the continuous-wave radar;
selecting one signal of the received I signal or the received Q signal by comparing magnitudes of the received I signal and the received Q signal;
performing fast Fourier transform (FFT) on the selected one signal to generate a fast-Fourier-transformed signal;
performing a frequency transform using a plurality of bases on the fast-Fourier-transformed signal to generate a plurality of magnitude responses of the frequency transform, each of the plurality of bases respectively having a predetermined phase; and
determining the heart rate based on the plurality of magnitude responses of the frequency transform.

2. The method of claim 1, further comprising:
performing zero-phase digital filtering on the received I signal and the received Q signal to generate a zero-phase-digital-filtered I signal and a zero-phase-digital-filtered Q signal, respectively,
wherein the selecting includes:
selecting the one signal by comparing magnitudes of the zero-phase-digital-filtered I signal and the zero-phase-digital-filtered Q signal.

3. The method of claim 1, wherein the performing of the frequency transform includes:
performing discrete cosine transform (DCT) using each of the plurality of bases.

4. The method of claim 1, wherein the determining of the heart rate includes:
determining, as the heart rate, a frequency for a largest magnitude response among the plurality of magnitude responses of the frequency transform.

5. The method of claim 1, wherein the determining of the heart rate includes:
extracting the plurality of magnitude responses of the frequency transform;
collecting maximum values of the magnitude responses and collecting frequency information of the maximum values through peak searching in a predetermined heart rate range; and determining, as the heart rate, a frequency with a largest value among the maximum values.

6. The method of claim 1, wherein the performing of the frequency transform includes:
performing a discrete transform using each of the plurality of bases respectively having the predetermined phase on the fast-Fourier-transformed signal.

7. The method of claim 1, wherein the performing of the frequency transform includes:
performing a discrete transform on the fast-Fourier-transformed signal using each of the plurality of bases respectively having the predetermined phase.

8. The method of claim 1, wherein the performing of the frequency transform includes: enhancing resolution of a heartbeat signal in a frequency spectrum obtained by performing a discrete transform by multiplying the fast-Fourier-transformed signal by one or more of the plurality of bases, wherein one or more predetermined phases are applied to the one or more of the plurality of bases.

9. A method for measuring a heart rate in real time based on a continuous-wave radar, the method comprising:
performing fast Fourier transform (FFT) on one signal of an in-phase (I) signal of a quadrature (Q) signal for a receive signal received through the continuous-wave radar to generate a fast-Fourier-transformed signal;
performing a frequency transform using a plurality of bases on the fast-Fourier-transformed signal to generate a plurality of magnitude responses of the frequency transform, each of the plurality of bases respectively having a predetermined phase; and
determining the heart rate based on the plurality of magnitude responses of the frequency transform.

10. The method of claim 9, wherein the performing of the frequency transform includes:
selecting the one signal by comparing magnitudes of the I signal and the Q signal; and
performing a discrete transform using each of the plurality of bases on the fast-Fourier-transformed signal.

11. The method of claim 10, wherein the performing of the frequency transform includes:
performing zero-phase digital filtering on the I signal and the Q signal to generate a zero-phase-digital-filtered I signal and a zero-phase-digital-filtered Q signal, respectively;
selecting the one signal by comparing magnitudes of the zero-phase-digital-filtered I signal and the zero-phase-digital-filtered Q signal; and
performing a discrete transform using each of the plurality of bases on the fast-Fourier-transformed signal.

12. The method of claim 10, wherein the determining of the heart rate includes:
extracting the plurality of magnitude responses of the frequency transform;
collecting maximum values of the magnitude responses and collecting frequency information of the maximum values through peak searching in a predetermined heart rate range; and
determining, as the heart rate, a frequency with a largest value among the maximum values.

13. The method of claim 10, wherein the performing of the frequency transform includes:
performing a discrete transform using each of the plurality of bases respectively having the predetermined phase on the fast-Fourier-transformed signal.

14. A radar system, comprising: a baseband receiving unit configured to remove a common mode direct current (DC) component and common mode noise from each of an in-phase (I) signal and a quadrature (Q) signal; and
a signal processing unit configured to
perform fast Fourier transform (FFT) on one signal of an I signal or a Q signal output from the baseband receiving unit to generate a fast-Fourier-transformed signal, and
perform a frequency transform using a plurality of bases on the fast-Fourier-transformed signal to generate a plurality of magnitude responses of the frequency transform, each of the plurality of bases respectively having a predetermined phase; and
determine a heart rate based on the plurality of magnitude response of the frequency transform.

15. The radar system of claim 14, wherein the baseband receiving unit removes the common mode DC component and the common mode noise by passing each of the I signal and the Q signal through an instrumentation amplifier.

16. The radar system of claim 14, wherein the signal processing unit
selects the one signal by comparing magnitudes of the I signal and the Q signal and
performs a discrete transform using each of the plurality of bases on the fast-Fourier-transformed signal.

17. The radar system of claim 14, wherein the signal processing unit
performs zero-phase digital filtering on the I signal and the Q signal to generate a zero-phase-digital-filtered I signal and a zero-phase-digital-filtered Q signal, respectively,
selects the one signal by comparing magnitudes of the zero-phase-digital-filtered I signal and the zero-phase-digital-filtered Q signal, and
performs a discrete transform using each of the plurality of bases on the fast-Fourier-transformed signal.

18. The radar system of claim 14, wherein the signal processing unit
extracts the plurality of magnitude responses of the frequency transform,
collects maximum values of the magnitude responses and collects frequency information of the maximum values through peak searching in a predetermined heart rate range, and
determines, as the heart rate, a frequency with a largest value among the maximum values.

19. The radar system of claim 14, wherein the signal processing unit performs a discrete transform using each of the plurality of bases respectively having the predetermined phase on the fast-Fourier-transformed signal.

20. The radar system of claim 14, wherein the signal processing unit enhances resolution of a heartbeat signal in a frequency spectrum obtained by performing a discrete transform by multiplying the fast-Fourier-transformed signal by one or more of the plurality of bases, wherein one or more predetermined phases are applied to the one or more of the plurality of bases.

* * * * *